United States Patent
Brown et al.

(10) Patent No.: US 6,933,297 B2
(45) Date of Patent: Aug. 23, 2005

(54) 7-CHLORO-4-HYDROXY-2-(2-PYRIDYLETHYL)-1,2,5,10-TETRAHYDROPYRIDAZINO[4,5-B]QUINOLINE-1,10-DIONE AND THE USE THEREOF FOR THE TREATMENT OF PAIN

(75) Inventors: Dean Gordon Brown, Wilmington, DE (US); Rebecca Ann Urbanek, Wilmington, DE (US); Megan Murphy, Wilmington, DE (US); Wenhua Xiao, Wilmington, DE (US); Frances Marie McLaren, Wilmington, DE (US); Edward Vacek, Wilmington, DE (US); Thomas Bare, West Chester, PA (US); Carey Lynn Horchler, Wilmington, DE (US); Christine Barlaam, Reims (FR); Gary Banks Steelman, Wilmington, DE (US); Vernon Alford, Raritan, NJ (US)

(73) Assignee: AstraZeneca AB, Sodertal (CH)

( * ) Notice: Subject to any disclaimer, the term of this patent is extended or adjusted under 35 U.S.C. 154(b) by 0 days.

(21) Appl. No.: 10/381,922

(22) PCT Filed: Sep. 28, 2001

(86) PCT No.: PCT/SE01/02125

§ 371 (c)(1), (2), (4) Date: Sep. 8, 2003

(87) PCT Pub. No.: WO02/26740

PCT Pub. Date: Apr. 4, 2002

(65) Prior Publication Data

US 2004/0053930 A1 Mar. 18, 2004

Related U.S. Application Data

(60) Provisional application No. 60/236,630, filed on Sep. 29, 2000.

(51) Int. Cl.$^7$ .................. A61K 31/5025; C07D 471/04
(52) U.S. Cl. ........................................ 514/248; 544/234
(58) Field of Search ........................... 514/248; 544/234

(56) References Cited

U.S. PATENT DOCUMENTS

2003/0153571 A1 * 8/2003 Brown et al. ................ 514/248
2004/0053929 A1 * 3/2004 Brown et al. ................ 514/248

FOREIGN PATENT DOCUMENTS

| EP | 0736531 | 10/1996 |
| WO | WO 9511244 | 4/1995 |
| WO | WO 0147524 | 7/2001 |

* cited by examiner

*Primary Examiner*—Emily Bernhardt
(74) *Attorney, Agent, or Firm*—Kenneth F. Mitchell

(57) ABSTRACT

A compound, 7-chloro-4-hydroxy-2-(2-pyridylethyl)-1,2,5,10-tetrahydropyridazino[4,5-b]quinoline-1,10-dione, its (−) enantiomer, its (+) enantiomer, pharmaceutically-acceptable salts thereof, a method for treating pain comprising administering a pain-ameliorating effective amount of the (−) enantiomer to an individual suffering from pain and pharmaceutical compositions containing the (−) enantiomer are disclosed.

4 Claims, No Drawings

7-CHLORO-4-HYDROXY-2-(2-PYRIDYLETHYL)-1,2,5,10-TETRAHYDROPYRIDAZINO[4,5-B] QUINOLINE-1,10-DIONE AND THE USE THEREOF FOR THE TREATMENT OF PAIN

RELATED APPLICATIONS

This is the National Phase of PCT Application No. PCT/SE01/02125 filed Sep. 28, 2001, which claims the priority of Provisional Application No. 60/236,630 filed Sep. 29, 2000.

FIELD OF THE INVENTION

This invention relates to the treatment or prevention of pain or nociception.

RELATED ART

Pain is a sensory experience distinct from sensations of touch, pressure, heat and cold. It is often described by sufferers by such terms as bright, dull, aching, pricking, cutting or burning and is generally considered to include both the original sensation and the reaction to that sensation. This range of sensations, as well as the variation in perception of pain by different individuals, renders a precise definition of pain difficult, however, many individuals suffer with severe and continuous pain.

Pain that is caused by damage to neutral structures is often manifest as a neural supersensitivity or hyperalgesia and is termed "neuropathic" pain. Pain can also be "caused" by the stimulation of nociceptive receptors and transmitted over intact neural pathways, such pain is termed "nociceptive" pain.

The level of stimulation at which pain becomes noted is referred to as the "pain threshold." Analgesics are pharmaceutical agents which relieve pain by raising the pain threshold without a loss of consciousness. After administration of an analgesic drug a stimulus of greater intensity or longer duration is required before pain is experienced. In an individual suffering from hyperalgesia an analgesic drug may have an anti-hyperalgesia effect. In contrast to analgesics, agents such as local anaesthetics block transmission in peripheral nerve fibers thereby blocking awareness of pain. General anaesthetics, on the other hand, reduce the awareness of pain by producing a loss of consciousness.

Tachykinin antagonists have been reported to induce antinociception in animals, which is believed to be analogous to analgesia in man (Maggi et al., J. Auton. Pharmacol. (1993) 13, 23–93). In particular, non-peptide NK-1 receptor antagonists have been shown to produce such analgesia. For example, the NK-1 receptor antagonist RP 67,580 produced analgesia with potency comparable to that of morphine (Garret et al., Proc. Natl. Acad. Sci. USA (1993) 88, 10208–10212).

The opioid analgesics are a well-established class of analgesic agents with morphine-like actions. Synthetic and semi-synthetic opioid analgesics are derivatives of five chemical classes of compound: phenanthrenes; phenylheptylamines; phenylpiperidines; morphinans; and benzomorphans. Pharmacologically these compounds have diverse activities, thus some are strong agonists at the opioid receptors (e.g. morphine); others are moderate to mild agonists (e.g. codeine); still others exhibit mixed agonist-antagonist activity (e.g. nalbuphine); and yet others are partial agonists (e.g. nalorphine). Whilst an opioid partial agonist such as nalorphine, (the N-alkyl analogue of morphine) will antagonize the analgesic effects of morphine, when given alone it can be a potent analgesic in its own right.

Of all of the opioid analgesics, morphine remains the most widely used, but, in addition to its therapeutic properties, it has a number of drawbacks including respiratory depression, decreased gastrointestinal motility (resulting in constipation), nausea and vomiting. Tolerance and physical dependence also limit the clinical uses of opioid compounds.

Aspirin and other salicylate compounds are frequently used in treatment to interrupt amplification of the inflammatory process in rheumatoid diseases and arthritis and temporarily relieve the pain. Other drug compounds used for these purposes include phenylpropionic acid derivatives such as Ibuprofen and Naproxen, Sulindae, phenyl butazone, coriticosteroids, antimalarials such as chloroquine and hydroxychloroquine sulfate, and fenemates (J. Hosp. Pharm., 36:622 (May 1979)). These compounds, however, are ineffective for neuropathic pain.

Available therapies for pain also have drawbacks. Some therapeutic agents require prolonged use before an effect is experienced by the patient. Other existing drugs have serious side effects in certain patients, and subjects must be carefully monitored to ensure that any side effects are not unduly threatening. Most existing drugs provide only temporary relief from pain and must be taken consistently on a dialy or weekly basis. With disease progression the amount of medication needed to alleviate the pain often increases, thus increasing the potential for adverse side effects.

NMDA receptors are defined by the binding of N-methyl-D-aspartate (NMDA) comprise a receptor/ion channel complex with several different identified binding domains. NMDA itself is a molecule structurally similar to glutamate (Glu) which binds at the glutamate binding suite and is highly selective and potent in activating the NMDA receptor (Walkins (1987): Olney (1989)).

Many compounds are known that bind at the NMDA/Glu binding site (for example CPP, DCPP-ene, CGP 40116, CGP 37849, GCS 19755, NPC, 12626, NPC, 17742, D-AP5, D-AP7, CGP 39551, CGP-43487, MDL-100,452, LY-274614, LY-233536, and LY233053). Other compounds, referred to as non-competitive NMDA antagonists, bind at other sites in the NMDA receptor complex (examples are phencyclidine, dizocilpine, ketamine, tiletamine, CNS 1102, dextromethorphan, memantine, kynurenic acid, CNQX, DNQX, 6,7-DCQX, 6,7-DCHQC, R(+)-HA-966, 7-chloro-kynurenic acid, 5,7-DCKA, 5-iodo-7-chloro-kynurenic acid, MDL-28,469, MDL-100,748, MDL-29,951, L-689,560, L-687,414, ACPC, ACPCM, ACPCF, areaino, diethylenetriamine, 1,10-diaminodecane, 1,12-diaminododecane, ifenprodil, and SL-82.0715). These compounds have been extensively reviewed by Rogawski (1992) and Massieu et al., (1993), and articles cited therein.

In addition to its physiological function, glutamate (Glu) can be neurotoxic, Glu neurotoxicity is referred to as "excitotoxicity" because the neurotoxic action of Glu, like its beneficial actions, is mediated by an excitatory process (Olney (1990); Choi (1992)). Normally, when Glu is released at a synaptic receptor, it binds only transiently and is then rapidly removed from the receptor by a process that transports it back into the cell. Under certain abnormal conditions, including stroke, epilepsy and CNS trauma, Glu uptake fails and Glu accumulates at the receptor resulting in a persistent excitation of electrochemical activity that leads to the death of neurons that have Glu receptors. Many neurons in the CNS have Glu receptors, so excitotoxicity can cause an enormous amount of CNS damage.

Acute excitotoxicity injury can occur as a result of ischemic events, hypoxic events, trauma to the brain or spinal cord, certain types of food poisoning which involve an excitotoxic poison such as domoic acid, and seizure-mediated neuronal degeneration, which can result from persistent epileptic seizure activity (status epilepticus). A large body of evidence has implicated the NMDA receptor as one receptor subtype through which Glu mediates a substantial amount of CNS injury, and it is well established that NMDA antagonists are effective in protecting CNS neurons against excitotoxic degeneration in these acute CNS injury syndromes (Choi (1988); Olney (1990)).

In addition to neuronal damage caused by acute insults, excessive activation of Glu receptors may also contribute to more gradual neurodegenerative processes leading to cell death in various chronic neurodegenerative diseases, including Alzheimer's disease, dihydrotrophic lateral sclerosis, AIDS dementia, Parkinson's disease and Huntington's disease (Olney (1990)). It is generally considered that NMDA antagonists may prove useful in the therapeutic management of such chronic diseases.

In the 1980's it was discovered that PCP (also known as "angel dust") acts at a "PCP recognition site" within the ion channel of the NMDA Glu receptor. PCP acts as a non-competitive antagonists that blocks the flow of ions through the NMDA ion channel. More recently it has become evident that drugs which act at the PCP site as non-competitive NMDA antagonists are likely to have psychotomimetic side effects. Further, it is now recognized that certain competitive and non-competitive NMDA antagonists can cause similar pathomorphological effects in rat brain (Olney et al., (1991); Hargreaves et al., (1993)). Such compounds also have psychotomimetic effects in humans (Kristensen et al., (1992); Herrling (1994); Grotta (1994)).

The glycine binding site of the NMDA receptor complex is distinguishable from the Glu and PCP binding sites. Also, it has recently been discovered that NMDA receptors occur as several subtypes which are characterized by differential properties of the glycine binding site of the receptor. Many compounds that bind at the NMDA receptor glycine site, useful for the treatment of stroke and neurodegenerative conditions, have been described in U.S. Pat. Nos. 5,604,227; 5,733,910; 5,599,814; 5,593,133; 5,744,471; 5,837,705 and 6,103,721.

SUMMARY OF THE INVENTION

It has now been discovered that a certain chiral compound which exhibits the property of binding to the NMDA receptor glycine site and utility for the amelioration of pain and particularly for the amelioration of neuropathic pain.

Therefore, the present invention provides a chiral compound according to structural diagram I and a method for the treatment of pain comprising administering a pain-ameliorating effective amount of such a compound.

It has been surprisingly discovered that the compound of structural diagram I, 7-chloro-4,10-dihydroxy-2-((S)-1-pyridin-2-yl-ethyl)-2H-pyridazino[4,5-b]quinoline-1-one, has profoundly different properties from those of the corresponding dextro-rotatory enantiomer. The results from the three biological tests indicate surprisingly different activities of the laevo-rotatory enantiomer when compared to either dextro-rotatory enantiomer or a racemic mixture of the two enantiomers.

First, measurement of the binding affinity shows that the laevo-rotatory enantiomer binds to the glycine receptor with a substantially higher affinity than the dextro-rotatory compound and exhibits a binding constant of about 190 nM compared to 3200 nM for the (+)-enantiomer.

Second, the laevo-rotatory enantiomer has different pharmacokinetic properties when compared to the racemic mixture. For example, the i.v. clearance of the racemate in the rat is much higher than that of the (−)-enantiomer. Tests show that the (−)-enantiomer is much more readily absorbed and is cleared at a slower rate.

Third, a test of the efficacy of the (−)-enantiomer in a neuropathic pain model shows that half the dose is required, 15 mg/kg compared to 30 mg/kg of the racemate to achieve a comparable effect. Additionally, and also unexpectedly, the (−)-enantiomer had a cumulative effect. When the dosing of a rat with the (−)-enantiomer was stopped, the animal continued to show a diminished response to a painful stimulus for at least a full day. This phenomenon was not observed with either the racemate or the (+)-enantiomer.

Advantageously, the (−)-enantiomer provides the potential for a treatment protocol that requires less compound and less frequent dosing than would be possible with the racemate or the (+)-enantiomer.

Thus, the present invention provides the chiral compound, 7-chloro-4,10-dihydroxy-2-((S)-1-pyridin-2-yl-ethyl)-2H-pyridazino[4,5-b]quinolin-1-one having a structure according to structural diagram I

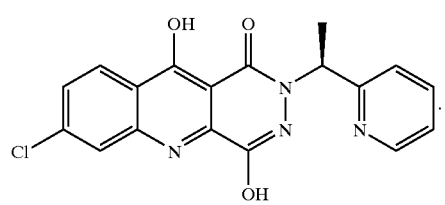

The invention also provides a method and pharmaceutical compositions for using the compound of structural diagram I as a therapeutic agent for the treatment of pain. Therefore, another aspect of the invention is a method for treating a subject suffering from pain comprising administering to said subject a pain-ameliorating effective amount of a compound in accord with structural diagram I.

Another embodiment of the invention is one where the method comprises treatment with a pharmaceutically-acceptable salt of 7-chloro-4,10-dihydroxy-2-((S)-1-pyridin-2-yl-ethyl)-2H-pyridazino[4,5-b]quinolin-1-one. A suitable pharmaceutically-acceptable salt is a methane-sulfonate.

Yet other aspects of the invention are pharmaceutical compositions which contain a compound in accord with structural diagram I; the use of compounds in accord with structural diagram I for the preparation of medicaments and pharmaceutical compositions, and a method comprising binding a compound of the invention to the NMDA receptor glycine site of a warm-blooded animal, such as a human being, so as to beneficially inhibit the activity of the NMDA receptor.

DETAILED DESCRIPTION OF THE INVENTION

Compounds of the invention are those within the scope of the generic description and particularly those compounds exemplified hereafter.

Suitable pharmaceutically-acceptable salts of compounds of the invention include acid addition salts such as methanesulphonate, fumarate, hydrochloride, hydrobromide, citrate, tris(hydroxymethyl)aminomethane, malcate and salts formed with phosphoric and sulphuric acid. In other embodiments, suitable salts are base salts such as an alkali metal salts for example sodium, alkaline earth metal salts for example calcium or magnesium, organic amine salts for example triethylamine, morpholine, N-methylpiperidino, N-ethylpiperidine, procaine, dibenzylamino, choline, N,N-dibenzylethylamine or amino acids such as lysino.

To use a compound of the invention or a pharmaceutically-acceptable salt thereof for the therapeutic treatment, which may include prophylactic treatment, of pain in mammals, which may be humans, the compound can be formulated in accordance with standard pharmaceutical practice as a pharmaceutical composition.

Suitable pharmaceutical compositions that contain a compound of the invention may be administered in conventional ways, for example by oral, topical, parenteral, buccal, nasal, vaginal or rectal administration or by inhalation. For these purposes a compound of the invention may be formulated by means known in the art into the form of, for example, tablets, capsules, aqueous or oil solutions, suspensions, emulsions, creams, ointments, gels, nasal sprays, suppositories, finely divided powders or acrosols for inhalation, and for parenteral use (including intravenous, intramuscular or infusion) sterile aqueous or oily solutions or suspensions or sterile emulsions. A preferred route of administration is orally by tablet or capsule.

In addition to a compound of the present invention a pharmaceutical composition of this invention may also contain one or more other pharmacologically-active agents, or such pharmaceutical composition may be simultaneously or sequentially co-administered with one or more other pharmacologically-active agents.

Pharmaceutical compositions of this invention will normally be administered so that a pain-ameliorating effective daily dose is received by the subject. The daily dose may be given in divided doses as necessary, the precise amount of the compound received and the route of administration depending on the weight, age and sex of the patient being treated and on the particular disease condition being treated according to principles known in the art. A preferred dosage regime is once daily.

A further embodiment of the invention provides a pharmaceutical composition which contains a compound of the structural diagram I as defined herein or a pharmaceutically-acceptable salt thereof, in association with a pharmaceutically-acceptable additive such as an excipient or carrier.

A yet further embodiment of the invention provide the use of a compound of the structural diagram I, or a pharmaceutically-acceptable salt thereof, in the manufacture of a medicament useful for binding to the NMDA receptor glycine site in a warm-blooded animal such as a human being.

Still another embodiment of the invention provides a method of binding a compound of the invention to the NMDA receptor glycine site of a warm-blooded animal, such as a human being, in need of treatment for pain, which method comprises administering to said animal an effective amount of a compound of structural diagram I or a pharmaceutically-acceptable salt thereof.

Definitions:
Generally in the methods, processes and examples described herein:

concentrations were carried out by rotary evaporation in vacuo;

operations were carried out at ambient temperature, that is in the range 18–26° C. and under a nitrogen atmosphere;

column chromatography (by the flash procedure) was performed on Merck Kieselgel silica (Art. 9385) unless otherwise stated;

yields are given for illustration only and are not necessarily the maximum attainable;

the structure of the end-products of the formula I were generally confirmed by NMR and mass spectral techniques, proton magnetic resonance spectra were determined in DMSO-$d_c$ unless otherwise stated using a Varian Gemini 2000 spectrometer operating at a field strength of 300 MHz; chemical shifts are reported in parts per million downfield from tetramethylsilane as an internal standard (8 scale) and peak multiplicities are shown thus: s, singlet; bs, broad singlet; d, doublet; AB or dd, doublet of doublets; t, triplet, dt, double of triplets, m, multiplet; bm, broad multiplet; fast-atom bombardment (FAB) mass spectral data were obtained using a Platform spectrometer (supplied by Micromass) run in electrospray and, where appropriate, either positive ion data or negative ion data were collected, in this application, $(M+H)^+$ is quoted; IR data was obtained with a Nicolet Avatar 360 FT-IR;

intermediates were not generally fully characterized and purity was in general assessed mass spectral (MS) or NMR analysis.

The following abbreviations and definitions when used, have the meanings, as follows:

| | |
|---|---|
| CDCl$_3$ | is deuterated chloroform; |
| CMC | is 1-cyclohexyl-3-(2-morpholinoethyl)carbodiimide metho-p-toluenesulfonate; |
| DCM | is dichloromethane; |
| DCU | is dicyclohexyl urea; |
| DHC | is 1,3-dicyclohexylcarbodiimide; |
| DMAP | is 4-(dimethylamino)pyridine; |
| DMF | is N,N-dimethylformamide; |
| DMSO | is dimethylsulphoxide; |
| m/s | is mass spectroscopy; |
| NMP | is N-methylpyrrolidinone; |
| NMR | is nuclear magnetic resonance; |
| p.o. | is per os; |
| THF | is tetrahydrofuran, and |
| t.i.d. | is three times daily. |

The examples and tests described herein are intended to illustrate but not limit the invention.

Assignment of absolute configuration is based on the literature values for a common intermediate, J. Org. Chem., 63, 2481–2487 (1998).

EXAMPLES:

Example 1:

7-Chloro-4,10-dihydroxy-2-((S)-1-pyridin-2-yl-ethyl)-2H-pyridazino[4,5-b]quinolin-1-one methanesulfonate, N-(1-Aza-2-(2-pyridyl)prop-1-enyl)(tert-butoxy) carboxyamide.

To a stirred solution of tert-butylcarbazate (2.18 g, 16.5 mmol) in THF (40 mL) was added 2-acetylpyridine (2.00 g, 16.5 mmol), followed by 3 drops of concentrated HCl. After 1 h, the reaction turned cloudy, and the solvent was removed in vacuo. The resultant solid was triturated with hexanes and filtered to give the title compound as a white solid (3.12 g, 80%). $^1$H NMR (300 MHz, DMSO-d$_6$): δ 1.49 (s, 9H); 7.38 (dd, 1H, J=4.8, 6.7 Hz); 7.94 (m, 1H); 7.99 (d, 1H, J=7.5 Hz); 8.58 (d, 1H, J=4.2 Hz); 10.04 (s, 1H).

(+/−)-(tert-Butoxy)-N-[(2-pyridylethyl)amino]carboxamide.

N-(1-Aza-2-(2-pyridyl)prop-1-enyl)(tert-butoxy)carboxamide (2.0 g, 8.5 mmol) was dissolved in methyl alcohol (80 mL) and placed in a Parr shaker bottle. To this was added 10% palladium-on-carbon (850 mg) and the reaction was hydrogenated at 40 psi for 24 h. The mixture was filtered through diatomaceous earth, which was washed with methyl alcohol (3×100 mL). The combined filtrate and washes were concentrated in vacuo. The title compound formed an oil (1.8 g) and was used in the following reaction without further purification. $^1$H NMR (300 MHz, DMSO-d$_6$): δ 1.19 (d, 3H, J=6.6 Hz); 1.33 (s, 9H); 4.11 (m, 1H); 4.79 (m, 1H); 7.22 (m, 1H); 7.49 (d, 1H, J=7.8 Hz); 8.22 (m, 1H, J=1.5, 2.4 Hz); 8.49 (d, 1H, J=4.2 Hz).

(−)-(tert-Butoxy)-N-[(2-pyridylethyl)amino]carboxamide.

The racemic mixture was subjected to chiral HPLC preparatory chromatography using CIHRALPAK-AD column (5 cm×50 cm). Approximately 10 g was resolved giving 4.5 g of peak 1 (>99% ee) and 4.7 g of peak 2 (98.6% ee) using acetonitrile as solvent. Peak 1 (t$_R$=5.07 min) had a (−) rotation and was identified as the title compound. The other enantiomer was obtained as peak 2 (t$_R$=6.15 min) with a (+) rotation. Characterization of Peak 1: $^1$H NMR (300 MHz, DMSO-d$_6$): δ 1.19 (d, 3H, J=6.6 Hz); 1.33 (s, 9H); 4.11 (m, 1H); 4.79 (m, 1H); 7.22 (m, 1H); 7.49 (d, 1H, J=7.8 Hz); 8.22 (m, 1H, J=1.5, 2.4 Hz); 8.49 (d, 1H, J=4.2 Hz). $[α]_D^{20}$=−128.78, (c=0.49). For opposite enantiomer $[α]_D^{20}$=+134.45, (c=0.49, MeOH).

Dimethyl 7-chloro-4-hydroxyquinoline-2,3-dicarboxylate:

A stirred mixture of methyl 2-amino-4-chlorobenzoate (2.50 g, 13.5 mmol) and dimethyl acetylene dicarboxylate (2.05 g, 14.4 mmol) in tert-butanol (22 ml) was refluxed for 7 hours under a nitrogen atmosphere. After adding additional dimethyl acetylenedicarboxylate (1.16 g, 8.13 mmol) and refluxing another 2.5 hours, the reaction mixture was allowed to cool to room temperature and potassium tert-butoxide (1.56 g, 13.9 mmol) was added in one portion. A precipitate formed and the resulting mixture was refluxed for 1.5 hours. The mixture was cooled to room temperature and filtered to separate the solids, which were washed with tert-butanol and diethyl ether. The solids were dissolved in water and acidified with 1 N sulfuric acid to form a precipitate. The resulting mixture was extracted with DCM and the combined extracts were washed with brine and water, dried over MgSO$_4$, filtered and concentrated to give a green solid. Recrystallization of this material from methanol provided the title compound (1.15 g, 47%) as an off-white solid, mp 232–233° C.; MS (Cl): 296 (M+H). Analysis for C$_{13}$H$_{10}$ClNO$_5$: Calc'd: C, 52.81; H, 3.41; N, 4.74; Found: C, 52.75; H, 3.47; N, 4.69.

3-Carbomethoxy-7-chloro-4-hydroxyquinoline-2-carboxylic acid:

To a stirred suspension of dimethyl 7-chloro-4-hydroxyquinoline-2,3-dicarboxylate (1.0 g, 3.38 mmol) in water (20 mL) was added an aqueous solution of sodium hydroxide (0.27 g, 6.75 mmol). Upon addition, the suspension dissolved. The reaction mixture was warmed to 60° C. for 1 hour. After this time the reaction was cooled to room temperature and acidified with concentrated hydrochloric acid. The product was then extracted into diethyl ether and ethyl acetate. The organic extracts were dried over MgSO$_4$, filtered and concentrated in vacuo to provide the title compound as a solid (900 mg). This material was purified by recrystallization employing an ethyl acetate/hexane co-solvent system to provide the title compound (571 mg, 60%) as a white solid mp 296° C. (dec); MS (Cl)=238 (M+H). Analysis for C$_{12}$H$_8$NO$_5$Cl·0.45 CH$_3$CO$_2$CH$_2$CH$_3$·0.10 H$_2$O: Calc'd: C, 51.30; H, 3.68; N 4.34, Found: C, 51.28; H, 3.62; N 3.97 $^1$H NMR 8.22 (d, J=8.7 Hz, 1H), 7.92 (d, J=1.8 Hz, 1H), 7.28 (dd, J=8.7, 1.8 Hz, 1H), 3.90 (s, 3H).

3-Carbomethoxy-2-pyrrolidinocarbamide-7-chloro-4-hydroxyquinoline;

To a suspension of 3-carbomethoxy-7-chloro-4-hydroxyquinoline-2-carboxylic acid (2.25 g, 8.0 mmol) in THF (20 mL) at ambient temperature under a N$_2$ atmosphere was added DHC (1.65 g, 8.0 mmol) and pyrrolidine (0.596 g, 8.4 mmol). The reaction was stirred room temperature for 15 hours after which time the by-product urea was removed via filtration. The desired product was purified via flash column chromatography employing 5% methanol in chloroform to provide the title compound (2.52 g, 94.3%) as a tan solid, mp=215° C.; MS (CI): 335 (M+H). 300 MHz $^1$H NMR (DMSO-d$_6$): 8.12 (d, J=8.7 Hz, 1H), 7.60 (d, 1H, J=1.8 Hz), 7.47 (dd, 1H, J=8.8, 2.0 Hz), 3.69 (s, 3H), 3.40–3.49 (m, 2H), 3.27–3.33 (m, 2H), 1.80–1.96 (m, 4H).

7-Chloro-4-oxo-2-(pyrrolidinylcarbonyl)hydroquinoline-3-carboxylic acid:

To a suspension of 3-carbomethoxy-2-pyrrolidinocarbamide-7-chloro-4-hydroxy quinoline (2.52 g, 7.5 mmol) in de-ionized water (40 mL) was added dropwise a solution (20 mL) of an aqueous potassium hydroxide (882 mg, 15.75 mmol). Upon complete addition, the reaction was warmed to 60° C. After 3 hours, the reaction was filtered to remove a small amount of insoluble material. The filtrate was then acidified to pH=1 which yield a white precipitate. The solid was isolated by vacuum filtration, washed with water, and dried at 30° C. in vacuo for 16 hours. This provided the title compound (1.5 g, 64%) as a white solid, mp=225.8° C.; MS (CI): 321 (M+H). 300 MHz $^1$H NMR (DMSO-d$_6$): δ 8.28 (d, J=8.8 Hz, 1H), 7.77 (s, 1H), 7.64 (d, 1H, J=8.7), 3.52–3.57 (m, 2H), 3.17–3.19 (m, 2H), 1.83–1.98 (m, 4H).

(−)-N-[(tert-Butoxy)carbonylamino][7-chloro-4-oxo-2-(pyrrolidinylcarbonyl)3-hydroquinolyl]-N-(2-pyridylethyl)carboxamide.

To a stirred slurry of 7-chloro-4-oxo-2-(pyrrolidinylcarbonyl)hydroquinoline-3-carboxylic acid (2.82 g, 8.79 mmol) in THF (100 mL) was added CMC (4.46 g, 10.5 mmol) and the reaction was stirred for five minutes. To this mixture a solution of (−)-(tert-butoxy)-N-[(2-pyridylethyl)amino]carboxamide (2.25 g, 9.49 mmol) and DMAP (0.160 g, 1.30 mmol) in THF (20 mL) was added dropwise. The mixture was stirred at room temperature for 45 minutes and then refluxed overnight. The cooled solution was filtered and the collected insolubles washed with DCM (2×150 mL). The combined filtrate and washes were concentrated in vacuo to dryness. The resultant yellow foam was subjected to chromatography (silica gel, 95/5 chloroform/methyl alcohol) to give the title compound as a yellow foam (4.6 g, 97%). $[α]_D^{20}$=−30.61, (c=0.49, MeOH).

7-Chloro-4,10-dihydroxy-2-((S)-1-pyridin-2-yl-ethyl)-2H-pyridazino[4,5-b]quinolin-1-one methanesulfonate.

To a stirred solution of (−)-N-[(tert-butoxy)carbonylamino][7-chloro-4-oxo-2-(pyrrolidinylcarbonyl)(3-hydroquinolyl]-N-(2-pyridinylethyl)carboxamide (4.62 g, 8.55 mmol) in THF (100 mL) was added methanesulfonic acid (18 mL) and the reaction was stirred overnight. The volatiles wee removed in vacuo and to the resultant oil was added diethyl ether (150 mL). The mixture was vigorously stirred for ten minutes and then allowed to stand until two layers formed. The top layer was documented away to leave a brown oil. Water (50 mL) was added to the oil and the mixture stirred until a fine yellow precipitate formed. This precipitate was filtered to give a tan solid. This material was washed with diethyl ether, and then sonicated twice in 20 mL of 7/1 diethyl ether/methyl alcohol for fifteen minutes and filtered. The insoluble materials were collected, washed with the same solvent system and dried to give the title compound (1.70 g, 56%) as an off-white powder. $^1$H NMR (300 MHz, DMSO-$d_6$): δ 1.77 (d, 3H, J=6.9 Hz); 2.34 (s, 3H, $CH_3SO_3H$); 6.41 (q, 1H, J=6.9 Hz); 7.44 (d, 1H, J=8.7 Hz); 7.80 (s, 1H); 7.87 (m, 2H); 7.96 (m, 1H); 8.02 (d, 1H, J=8.7 Hz); 8.43 (app t, 1H, J=7.5 Hz); 8.86 (d, 1H, J=5.1 Hz); 11.98 (s, 1H); 12.80 (s, 1H). $[α]_D^{20}$=−175.28, (c=0.49, MeOH). The enantiomeric excess was determined to be >95% by chiral shift reagent (1R,1S)-(−)-N-methylephedrine or $d^H$-(S-(+)-2,2,2-trifluoro-1-(9-anthryl)ethanol)). Calc'd. for $C_{18}H_{13}ClN_4O_3·CH_3SO_3H·H_2O$: C, 47.25; H, 3.96; N, 11.60; Found: C, 47.26; H, 3.67; N, 11.50.

Example 2:

7-Chloro-4,10-dihydroxy-2-((R)-1-pyridin-2-yl-ethyl)-2H-pyridazino[4,5-b]quinolin-1-one methanesufonate.

(+)-N-[(tert-Butoxy)carbonylamino][7-chloro-4-oxo-2-(pyrrolidinylcarbonyl)(3-hydroquinolyl]-N-(2-pyridylethyl) carboxamide.

To a stirred slurry of 7-chloro-4-oxo-2-(pyrrolidinylcarbonyl)hydroquinoline-3-carboxylic acid, Example 1, (2.57 g, 8.03 mmol) in THF (100 mL) was added CMC (4.07 g, 9.63 mmol) and the reaction was stirred for five minutes. To this mixture a solution of (+)-(tert-butoxy)-N-[(2-pyridylethyl)amino]carboxamide (2.0 g, 8.43 mmol) and DMAP (0.160 g, 1.30 mmol) in THF (20 mL) was added dropwise. The mixture was stirred at room temperature for 45 minutes and then refluxed overnight. The cooled solution was filtered and the collected insolubles washed with DCM (2×150 mL). The combined filtrate and washes were concentrated in vacuo to dryness. The resultant yellow foam was subjected to chromatography (silica gel, 95/5 chloroform/methyl alcohol) to give the title compound as a yellow foam (4.0 g, 95%). $[α]_D^{20}$=+54.27, (c=0.51, MeOH).

7-Chloro-4,10-dihydroxy-2-((R)-1-pyridin-2-yl-ethyl)-2H-pyridazinyo[4,5-b]quinolin-1-one methanesulfonate.

To a stirred solution of (+)-N-[(tert-butoxy)carboxy)carbonylamino][7-chloro-4-oxo-2-(pyrrolidinylcarbonyl)(3-hydroquinolyl]-N-(2-pyridylethyl)carboxamide (4.0 g, 7.40 mmol) in THF (100 mL) methanesulfonate acid (20 mL) was added and the reaction was stirred overnight. The volatiles were removed in vacuo and diethyl ether (150 mL) was added to the resultant material. The mixture was vigorously stirred for ten minutes and then allowed to stand until two layers formed. The top layer was decanted away to leave a brown oil. To this oil was added water (50 mL) and the mixture stirred until a fine yellow precipitate formed. This precipitate was filtered to give a tan solid. This material was washed with diethyl ether, and then sonicated twice in 20 mL of 12/1 diethyl ether/methyl alcohol for fifteen minutes and filtered. The insoluble materials were collected, washed with the same solvent system and dried to give the title compound (1.31 g, 48%) as an off-white powder. $^1$H NMR (300 MHz, DMSO-$d_6$): δ 1.77 (d, 3H, J=6.9 Hz); 2.34 (s, 3H, $CH_3SO_3H$); 6.41 (q, 1H, J=6.9 Hz); 7.44 (d, 1H, J=8.7 Hz); 7.82 (m, 2H); 7.91 (d, 1H, J=7.8 Hz); 8.02 (d, 1H, J=8.7 Hz); 8.39 (app t, 1H, J=7.5 Hz); 8.84 (d, 1H, J=5.1 Hz); 11.98 (s, 1H); 12.80 (s, 1H). $[α]_D^{20}$=+173.86, (c=0.49, MeOH). The enantiomeric excess was determined to be >95% with the chiral shift reagent (1R,1S)-(−)-N-methylephedrine or $d^{11}$-(S-(+)-2,2,2-trifluoro-1-(9-anthryl)ethanol)). Calc'd. for $C_{18}H_{13}ClN_4O_3·CH_3SO_3H·0.9\ H_2O$: C, 47.43; H, 3.93; N, 11.64; Found: C, 47.84; H, 3.70; N, 11.60.

Example 3:

(+/−)-7-Chloro-4,10-dihydroxy-2(-1-pyridin-2-yl-ethyl)-2H-pyridazino[4,5-b]quinolin-1-one methanesulfonate.

N-(1-Aza-2-(2-pyridyl)prop-1-cnyl)(tert-butoxy) carboxamide,

To a stirred solution of tert-butylcarbazate (2.18 g, 16.5 mmol) in THF (40 mL) was added 2-acetylpyridine (2.00 g, 16.5 mmol), followed by 3 drops of concentrated hydrochloric acid. After 1 h, the reaction turned cloudy, and the solvent was removed in vacuo. The resultant solid was triturated with hexanes and filtered to give the title compound as a white solid (3.12 g, 80%). $^1$H NMR (300 MHz, DMSO-$d_6$): δ 1.49 (s, 9H); 7.38 (dd, 1H, J=4.8, 6.7 Hz); 7.94 (m, 1H); 7.99 (d, 1H, J=7.5 Hz); 8.58 (d, 1H, J=4.2 Hz); 10.04 (s, 1H).

(+/−)-(tert-Butoxy)-N-[(2-pyridylethyl)amino] carboxamide,

N-(1-Aza-2-(2-pyridyl)prop-1-enyl)(tert-butoxy) carboxamide (2.0 g, 8.5 mmol) was dissolved in methyl alcohol (80 mL) and placed in a Parr shaker bottle. To this was added 10% palladium-on-carbon (850 mg) and the reaction was hydrogenated at 40 psi for 24 h. The mixture was filtered through diatomaceous earth, which was washed with methyl alcohol (3×100 mL). The combined filtrate and washes were concentrated in vacuo. The resultant oil (cn. 1.8 g) was used in the following reaction without further purification. $^1$H NMR (300 MHz, DMSO-$d_6$): δ 1.19 (d, 3H, J=6.6 Hz); 1.33 (s, 9H); 4.11 (m, 1H); 4.79 (m, 1H); 7.22 (m, 1H); 7.49 (d, 1H, J=7.8 Hz); 8.22 (m, 1H, J=1.5, 2.4 Hz); 8.49 (d, 1H, J=4.2 Hz).

(+/−)-N-[(tert-Butoxy)carbonylamino][7-chloro-4-oxo-2-(pyrrolidinylcarbonyl)(3-hydroquinolyl]-N-(2-pyridylethyl) carboxamide, To a stirred slurry of 7-chloro-4-oxo-2-(pyrrolidinylcarbonyl)hydroquinoline-3-carboxylic acid, Example 1, (2.43 g, 7.57 mmol) in THF (100 mL) was added CMC (3.69 g, 8.72 mmol) and the reaction was stirred for five minutes. To this mixture was added dropwise a solution of (+/−)-(tert-butoxy)-N-[(2-pyridylethyl)amino] carboxamide (1.8 g, 7.59 mmol) and DMAP (0.160 g, 1.30 mmol) in THF (20 mL). The mixture was stirred at room temperature for 45 minutes and then refluxed overnight. The cooled solution was filtered and the collected insolubles washed with DCM (2×150 mL). The combined filtrate and washes were concentrated in vacuo to dryness. The resultant yellow foam was subjected to chromatography (silica gel, 95/5 chloroform/methyl alcohol) to give the title compound as a yellow foam (3.3 g, 81%).

(+/−)-7-Chloro-4,10-dihydroxy-2-(-1-pyridin-2-yl-ethyl)-2H-pyridazino[4,5-b]quinolin-1-one methane-sulfonate.

To a stirred solution of (+/−)-N-[(tert-butoxy) carbonylamino][7-chloro-4-oxo-2-(pyrrolidinylcarbonyl)(3- hydroquinolyl]-N-(2-pyridylethyl)carboxamide (3.0 g, 5.56 mmol) in THF (100 mL) was added methanesulfonic acid (15 mL) and the reaction was stirred overnight. The volatiles were removed in vacuo and the resultant oil was poured on to crushed ice. A fine precipitate formed which was filtered to give an orange solid. This material was washed with diethyl ether, and then sonicated in 20 mL of 1/1 diethyl ether/methyl alcohol for fifteen minutes and filtered. The collected solids were sonicated again in 85 mL of the same solvent system for an additional fifteen minutes. The insoluble materials were collected, washed with the same solvent system and dried at 55° C. for 12 h to give the title compound (1.29 g, 48%) as an off-white powder (m.p. >290° C.). $^1$H NMR (300 MHz, DMSO-d$_6$): δ 1.77 (d, 3H, J=6.9 Hz); 2.34 (s, 3H, CH$_3$SO$_3$H); 6.38 (q, 1H, J=6.9 Hz); 7.44 (dd, 1H, J=1,5, 8.7 Hz); 7.82 (m, 2H); 7.90 (d, 1H, J=8.1 Hz); 8.04 (d, 1H), J=8.7 Hz); 8.38 (appt, 1H, J=7.5 Hz); 8.82 (d, 1H, J=5.1 Hz); 11.98 (s, 1H); 12.80 (s, 1H). Calc'd. for C$_{18}$H$_{13}$ClN$_4$O$_3$·CH$_3$SO$_3$H·H$_2$O: C, 47.25; H, 3.96; N, 11.60. Found: C, 47.26; H, 3.67; N, 11.50.

Example 4:

7-Chloro-4,10-dihydroxy-2-((S)-1-pyridin-2-yl-ethyl)-2H-pyridazino[4,5-b]quinolin-1-one, free base.

Preparation of the free base title compound was achieved as follows. The methanesulfonate salt from Example 1 (3 g, 6.23 mmol) was slurried in 100 mL of distilled water and heated to reflux. Sodium bicarbonate solution was carefully added (0.523 g, 6.23 mmol, dissolved in 5 mL distilled water) and the mixture cooled to room temperature. The solids were collected by vacuum filtration, washed with diethyl ether (2×30 mL) and dried under vacuum (60° C., 200 mtorr) to give the title compound as a white solid (2.14 g, 86% yield). $^1$H NMR (300 MHz, DMSO-d$_6$): δ 1.70 (d, 3H, J=6.9 Hz); 6.22 (q, 1H, J=6.9 Hz); 7.24 (m, 2H); 7.41 (d, 1H, 8.4 Hz); 7.73 (t, 1H, J=7.8 Hz); 8.03 (s, 1H); 8.15 (d, 1H, J=8.4 Hz); 8.51 (d, 1H, J=4.5 Hz); 11.88 (br s, 1H); 12.47 (br s, 1H), Calc'd. for C$_{18}$H$_{13}$ClN$_4$O$_3$·1.65 H$_2$O: C, 54.25; H, 4.12; N, 14.06; Found: C, 54.25; H, 4.14; N, 13.95.

Example 5:

Anionic salts—representative examples

Anionic salts of (−)-7-chloro-4-hydroxy-2-(2-pyridylethyl)-1,2,5,10-tetrahydropyridazino[4,5-b]quinoline-1,10-dione were prepared as follows. Free base (0.25 g, 0.6 mmol) from Example 4 was slurried in dry methyl alcohol (4 mL). To this is added either an amine base or an inorganic base (1.05 equiv) and the mixture heated to reflux. In some cases, the material dissolved at higher temperatures and recrystallized upon cooling. If the material did not recrystallize upon cooling, a portion of isopropyl alcohol was added to facilitate the process. If the material did not dissolve in hot methanol, hot water was added during reflux to facilitate solubilization. If this was unsuccessful, the material was cooled, filtered, collected and used as is. Once the solid material was isolated it was dried in vacuo (200 mtorr) at 65° C. for 4 h or until residual solvent was gone. Analysis of chiral purity was done as described for the methanesulfonate salt. No loss of optical purity was noted.

Table 1 shows the structure and physical properties of several anionic salts.

TABLE 1

| Salt form | Base | Solvent | Analysis |
|---|---|---|---|
| Diethanol-amine | Diethanol-amine | methyl alcohol | $^1$H NMR (300 MHz, DMSO-d$_6$) δ 1.63 (d, 3H, J = 7.0 Hz); 2.89 (t, 4H, J = 5.5 Hz); 3.59 (t, 4H, J = 5.5 Hz); 6.20 (q, 1H, J = 7.0 Hz); 7.12 (d, 1H, J = 8.0 Hz); 7.18 (m, 1H); 7.32 (dd, 1H, J = 1.8, 8.7 Hz); 7.65 (t, 1H, 7.7 Hz); 8.07 (s, 1H); 8.13 (d, 1H, J = 8.7 Hz); 8.48 (d, 1H, J = 4.6 Hz). Calc'd. for C$_{18}$H$_{13}$ClN$_4$O$_3$·C$_4$H$_{11}$NO$_2$; C, 55.76; H, 5.10; N, 14.78 Found: C, 55.83; H, 4.92; N, 14.73. |
| Piperazine | piperazine | methyl alcohol, water (1:1) | $^1$H NMR (300 MHz, DMSO-d$_6$) δ 1.65 (d, 3H, J = 7.0 Hz); 2.87 (s, 4H); 6.19 (q, 1H, J = 7.0 Hz); 7.15 (d, 1H, J = 8.0 Hz); 7.21 (m, 1H); 7.37 (dd, 1H, J = 1.8, 8.7 Hz), 7.65 t, 1H, 7.7 Hz); 8.06 (s, 1H); 8.13 (d, 1H, J = 8.7 Hz); 8.48 (d, 1H, J = 4.6 Hz). Calc'd, for C$_{18}$H$_{13}$ClN$_4$O$_3$·0.5 C$_4$H$_{10}$N$_2$·0.75H$_2$O; C, 56.47; H, 4.62; N, 16.46 Found: C, 56.60; H, 4.58; N, 16.35. |
| Sodium | Sodium hydroxide (1N aqueous) | methyl alcohol, water, isopropyl alcohol to initiate crystal formation | $^1$H NMR (300 MHz, DMSO-d$_6$) δ 1.65 (d, 3H, J = 7.0 Hz); 6.25 (q, 1H, J = 7.0 Hz); 7.13 (d, 1H, J = 8.0 Hz); 7.21 (m, 1H); 7.33 (dd, 1H, J = 1.8, 8.7 Hz), 7.65 (t, 1H, 7.7 Hz); 8.09 (s, 1H); 8.15 (d, 1H, J = 8.7 Hz); 8.49 (d, 1H, J = 4.6 Hz). |
| Potassium | Potassium Hydroxide (1N aqueous) | methyl alcohol, water | $^1$H NMR (300 MHz, DMSO-d$_6$) δ 1.65 (d, 3H, J = 7.0 Hz); 6.21 (q, 1H, J = 7.0 Hz); 7.13 (d, 1H, J = 8.0 Hz); 7.22 (m, 1H); 7.36 (dd, 1H, J = 1.8, 8.7 Hz), 7.67 (t, 1H, 7.7 Hz); 8.05 (s, 1H); 8.13 (d, 1H, J = 8.7 Hz); 8.49 (d, 1H, J = 4.6 Hz). |

Example 6:

Cationic salts—representative examples

Cationic salts of (−)-7-chloro-4-hydroxy-2-(2-pyridylethyl)-1,2,5,10-tetrahydropyridazino[4,5-b]quinoline-1,10-dione were prepared as follows. Free base (0.5 mmol) from Example 3 was slurried in methyl alcohol and heated to reflux. The desired acid was added (0.5 mmol) and the solution was refluxed for fifteen minutes. Upon cooling to room temperature either a precipitate or a clear solution was obtained. If a precipitate formed, this was recovered by filtration, washed with methanol and dried overnight at 50° C. in vacuo (0.05–0.1 mbar) (Method A). If traces of solvent were detectable, the material was resubjected to overnight drying at 70–80° C. in vacuo (0.05–0.1 mbar). If a clear solution was obtained, the solution was concentrated and any formed solid was dissolved in ethyl alcohol or a mixture of ethyl alcohol/methyl alcohol, heated to get a clear solution and cooled to form crystals (Method B). The crystals were filtered washed with ethanol and diethyl ether and dried as described above.

Table 2 shows the structure and physical properties of several unionic salts.

TABLE 2

| Salt form | Acid | Method | Analysis |
|---|---|---|---|
| Tartrate | Tartaric acid | A | $^1$H NMR (300 MHz, DMSO-d$_6$) δ 1.71 (d, 3H, J = 7.0 Hz); 4.32 (s, 1H); 5.07 (br s, 1H); 6.22 (q, 1H, J = 7.0 Hz); 7.25 (m, 2H); 7.41 (d, 1H, 8.7 Hz), 7.73 (t, 1H, J = 7.7 Hz); 8.03 (s, 1H); 8.15 (d, 1H, J = 8.7 Hz); 8.50 (d, 1H, J = 4.6 Hz), 11.91 (s, 1H); 12.55 (br s, 2H). Calc'd for C$_{18}$H$_{13}$ClN$_4$O$_3$·C$_4$H$_6$O$_6$·1.55H$_2$O: C, 48.33; H, 4.07; N, 10.25; Found: C, 48.45; H, 4.26; N, 10.05 |
| Citrate | Citric acid | A | $^1$H NMR (300 MHz, DMSO-d$_6$) δ 1.71 (d, 3H, J = 7.0 Hz); 2.65 (d, 2H, J = 15.3 Hz); 2.76 (d, 2H, J = 15.3 Hz) 6.23 (q, 1H, J = 7.0 Hz); 7.25 (m, 2H); 7.43 (d, 1H, J = 8.7 Hz), 7.73 (t, 1H, J = 7.7 Hz); 8.03 (s, 1H); 8.15 (d, 1H, J = 8.7 Hz); 8.50 (d, 1H, J = 4.6 Hz), 11.91 (s, 1H); 12.48 (br s, 2H). Calc'd. for C$_{18}$H$_{13}$ClN$_4$O$_3$·C$_4$H$_8$O$_7$·1.75H$_2$O: C, 51.35; H, 4.16; N, 11.74; Found: C, 51.29; H, 4.10; N, 11.70. |
| Hydrochloride | HCl (1 N aqueous) | A | $^1$H NMR (300 MHz, DMSO-d$_6$) δ 1.76 (d, 3H, J = 7.0 Hz); 4.58 (br); 2.76 (d, 2H, J = 15.3 Hz) 6.33 (q, 1H, J = 7.0 Hz); 7.42 (d, 1H, J = 8.7 Hz), 7.70 (m, 2H); 7.93 (d, 1H, J = 1.8 Hz); 8.08 (d, 1H, J = 8.7 Hz); 8.23 (t, 1H, J = 7.8 Hz); 8.76 (d, 1H, J = 4.6 Hz), 12.67 (s, 1H). Calc'd. for C$_{18}$H$_{13}$ClN$_4$O$_3$·1.3HCl·2H$_2$O: C, 47.81; H, 4.08; N, 12.39; Found: C, 47.76; H, 4.21; N, 12.28. |
| Ethanesulfonate | Ethanesulfonic acid | B | $^1$H NMR (300 MHz, DMSO-d$_6$) δ 1.06 (t, 3H, J = 7.2 Hz); 1.76 (d, 3H, J = 7.0 Hz); 2.40 (q, 2H, J = 7.2 Hz); 6.43 (q, 1H, J = 7.0 Hz); 7.43 (dd, 1H, J = 1.8, 8.7 Hz); 7.78 (s, 1H); 7.85 (t, 1H, J = 7.7 Hz); 7.96 (d, 1H, J = 7.7 Hz); 8.03 (d, 1H, J = 8.7 Hz); 8.41 (t, 1H, J = 7.7 Hz); 8.56 (d, 1H, J = 4.6 Hz), 11.99 (s, 1H); 12.86 (br s, 2H). Calc'd. for C$_{17}$H$_{13}$ClN$_4$O$_3$·1.1C$_2$H$_6$O$_3$S·0.1H$_2$O·C$_2$H$_5$OH: C, 49.42; H, 4.31; N, 11.08; Found: C, 49.53; H, 4.19; N, 10.98. |
| p-toluenesulfonate | p-toluenesulfonic acid | B | $^1$H NMR (300 MHz, DMSO-d$_6$) δ 1.76 (d, 3H, J = 7.0 Hz); 2.29 (s, 3H); 6.43 (q, 1H, J = 7.0 Hz); 7.10 (d, 2H, J = 8.7 Hz); 7.43 (m, 3H); 7.78 (s, 1H); 7.85 (t, 1H, J = 7.7 Hz); 7.95 (m, 1H); 8.03 (d, 1H, J = 8.7 Hz); 8.41 (t, 1H, J = 7.7 Hz); 8.86 (d, 1H, J = 4.6 Hz), 11.99 (s, 1H); 12.86 (br s, 2H). Calc'd. for C$_{18}$H$_{13}$ClN$_4$O$_3$·0.85C$_7$H$_9$O$_3$S·1.2H$_2$O: C, 55.38; H, 3.98; N, 14.35; Found: C, 55.50; H, 3.99; N, 14.14 |
| Benzenesulfonate | benzenesulfonic acid | B | $^1$H NMR (300 MHz, DMSO-d$_6$) δ 1.76 (d, 3H, J = 7.0 Hz); 6.43 (q, 1H, J = 7.0 Hz); 7.30 (m, 3H); 7.45 (dd, 1H, J = 1.8, 8.7 Hz); 7.59 (m, 2H); 7.73 (s, 1H); 7.90 (t, 1H, J = 7.7 Hz); 8.03 (m, 1H); 8.48 (t, 1H, J = 7.7 Hz); 8.89 (d, 1H, J = 4.6 Hz), 11.99 (s, 1H); 12.86 (br s, 2H). Calc'd. for C$_{18}$H$_{13}$ClN$_4$O$_3$·1.2C$_6$H$_6$O$_3$S: C, 54.19; H, 3.64; N, 10.03; Found: C, 54.48; H, 3.95; N, 9.80. |
| Maleate | maleic acid | A | $^1$H NMR (300 MHz, DMSO-d$_6$) δ 1.72 (d, 3H, J = 7.0 Hz); 6.42 (m, 2H); 7.28 (m, 2H); 7.42 (dd, 1H, J = 1.8, 8.7 Hz); 7.90 (t, 1H, 7.7 Hz); 8.02 (s, 1H); 8.14 (d, 1H, J = 8.7 Hz); 8.53 (d, 1H, J = 4.6 Hz), 11.93 (s, 1H); 12.54 (br s, 2H). |

Example 7:

7-Chloro-4,10-dihydroxy-2-((R)-1-pyridin-2-yl-ethyl)-2H-pyridazino[4,5-b]quinolin-1-one.

Preparation of the title compound as a free base may be achieved from the compound of Example 2, as described in Example 4.

Example 8:

(−)-(tert-Butoxy)-N-[(2-pyridylethyl)amino]carboxamide.

The title compound, used in Example 1, may be also prepared as follows:

(R)-1-(2-Pyridyl)-1-ethanol:

(R)-1-(2-Pyridyl)-1-ethanol, a chiral alcohol, was prepared by enzymatic resolution according to the procedure of Uenishi et al. *J. Org. Chem.* 63, 2481–2487 (1998).

(R)-1-(Pyridyl)-1-ethane methane sulfonate:

To a stirred solution of (R)-1-(2-pyridyl)-1-ethanol (0.30 g, 2.41 mmol) in methylene chloride (2.5 mL) at 0° C. was added triethylamine (0.37 g, 0.51 mL, 3.66 mmol) and N,N-dimethylaminopyridine (0.035 g, 0.28 mmol). Finally a solution of methanesulfonyl chloride (0.41 g, 0.28 mL, 3.60 mmol) in methylene chloride (2.5 mL) was added dropwise and the solution stirred for 1.5 h. The reaction was then poured on to cold sodium bicarbonate (sat. aqueous solution). An additional portion of methylene chloride (50 mL) was added to aid in the extraction. The organic layer was extracted with water (2×10 mL), then dried over Na$_2$SO$_4$. The organic layer was filtered and concentrated to give the title compound. The title compound was then used immediately in the next reaction (0.49 g, 100%). $^1$H NMR (300 MHz, CDCl$_3$): δ 1.76 (d, 3H, J=6.6 Hz); 2.94 (s, 3H); 5.79 (m, 1H); 4.79 (m, 1H); 7.30 (m, 1H); 7.47 (d, 1H, J=7.8 Hz); 7.77 (ddd, 1H, J=1.5, 7.8 Hz, 7.8 Hz); 8.49 (d, 1H, J=4.5 Hz).

(−)-(tert-Butoxy)-N-[(2-pyridylethyl)amino]carboxamide:

(−)-1-(Pyridyl)-1-ethane methane sulfonate (0.49 g, 2.41 mmol) was dissolved in anhydrous N,N-dimethylformamide (7 mL) under a nitrogen atmosphere. To the stirred solution was added N,N-diisopropylethylamine (0.47 g, 0.63 mL, 3.66 mmol) and tert-butyl carbazate (1.55 g, 11.7 mmol). The solution was kept at 90° C. for 6h at which point the reaction was cooled, diluted with ethyl acetate (50 mL), and then extracted with distilled water (3×10 mL). The organic layer was extracted with sodium chloride (15 mL, sat. aqueous solution) and dried over Na$_2$SO$_4$. The organic layer was then filtered and evaporated to yield a yellow oil. In a short time, the oil formed a tacky solid which was triturated with hexanes/diethyl ether (1:1, 2 mL total). A solid was then collected by filtration. The solid was then chromatographed on SiO$_2$ using 1:1 diethyl ether/hexanes to give the title compound (0.06 g). The solvent was removed from the remaining filtrates and these were subjected to chromatography on a separate column (using 1:1 diethyl ether/hexanes). The title compound was recovered from this column (0.09 g) and combined with the other material (0.154 g, 28% yield, 99% ee as determined by HPLC chromatography CHIRALCEL-OD column; eluents= hexane, ethyl alcohol, diethylamine 95:5:0.05; $t_x$=10.88. Opposite isomer $t_g$=9.62). This material was indistingushable from the (−) enatiomer described in Example 1.

TESTS FOR BIOLOGICAL FUNCTION:

Test A: Inhibition of binding of [$^3$H]-MDL105,519;

Binding of compounds to the NMDA receptor glycine site may be assessed by measuring the ability of test compounds to inhibit the binding of tritiated MDL105,519 to brain membranes bearing the receptor.

Rat Brain Membranes: The rat brain membranes used in the experiments were obtained from Analytical Biological Services Inc., and were prepared substantially in accordance with the method of B. M. Baron et al., *J. Pharmacol. Exp. Ther.* 250, 162 (1989). Briefly, fresh brain tissue including cerebral cortex and hippocampus from male Sprague Dawley rats was homogenized in 0.32 M sucrose and centrifuged at low speed to separate cellular membranes from other cellular components. The membranes were then washed 3 times using deionized water, followed by treatment with 0.04% Triton X-100. Finally, membranes were washed six times in 50 mM Tris citrate buffer, pH 7.4, and frozen at −80° C. until use.

[$^3$H]MDL105,519 (72 Ci/mmol) was purchased from Amersham. Cold MDL105,519 was purchased from Sigma/RBI. Binding assays were performed substantially in accordance with the protocol of B. M. Baron et al., *J. Pharmacol. Exp. Ther.* 279, 62 (1996), as follows. On the day of the experiment, brain membranes were thawed at room temperature and suspended in 50 mM tris acetate buffer, pH 7.4 ("TAB"). Seventy-five micro grams per milliliter protein (by using the BioRad dye) were used for competition binding. The experiments were carried out using 96-well plates. Membranes were incubated with 20 μL of compounds of various concentrations and 1.2 nM [$^3$H]MDL105,519 for 30 minutes at room temperature in a total volume of 250 μL. Non specific binding was determined by using 100 μM of unlabeled MDL105,519. The unlabeled MDL105,519 and compounds were dissolved as 12.5 mM stock solutions in DMSO. Final DMSO concentration in each well was kept below 1%, which concentration was found not to alter the binding results. After incubation, unbound [$^3$H]MDL105,519 was removed by filtration onto GF/B Unifilter plates using a Packard harvester. Filters were washed four times with ice cold TAB (total of 1.2 mL buffer). The plates were dried overnight at room temperature and bound radioactivity was measured on a Packard TopCount after the addition of 45 μL per well of the MICROSCINT O.

Human Brain Membranes: Human brain membranes were obtained from Analytical Biological Services Inc., and assays were performed as described for rat membranes.

Data analysis: Data was analyzed using a Microsoft Excel spreadsheet and GraphPad Prizm software and potency of compounds is expressed as the Ki (nM).

Test B: Formalin test:

The Formalin test is an assay that assesses the capacity of a compound to inhibit formalin-induced nociceptive behaviors in rats (D. Dubuisson, et al., *Pain* 4, 161–174 (1977); H. Wheeler-Aceto et al., *Psychopharmacology* 104, 35–44 (1991); T. J. Coderre, et al., *Pain* 54, 43–50 (1993)). In the test, two distinctive phases of formalin-induced behaviors are observed. A first phase response, caused by acute nociception to the noxious chemical (formalin) injected into the paw, occurs between zero and five minutes. A quiescent period of 5 to 15 min post injection follows. After the quiescent period a second phase response, caused by sensitization of the central neurons in the dorsal horn, occurs after 15 minutes and lasts up to 60 minutes. Sensitization of the central neurons in the spine augments a noxious afferent input and causes a stronger pain barrage to be transmitted to the brain. Therefore, inhibition of the second phase response indicates a central mechanism of drug action.

The procedure for the formalin test is as follows: male rats are placed in a plexiglass chamber and observed for 30–45 min. to observe their baseline activity. Animals are either pretreated with vehicle or with different doses of a test compound. Animals are dosed with vehicle or test compound three hours prior to injection of 0.05 mL of sterile 1% formalin under the dorsal skin of a hind paw. The number of paw flinches (responses) during the first phase (0–5 min.) and the second phase (20–35 min.) are scored and recorded. Flinch response is compared with the mean score of a saline control group and calculated as percentage inhibition. The $ED_{50}$ is the dose of compound which produces 50% inhibition of nociceptive response in the first or second phase response. First phase responses may be inhibited by compounds that act peripherally and by compounds that act centrally. Second phase response are inhibited by centrally active compounds.

% inhibition of nociceptive response =100×(number of responses to vehicle group—number of responses in compound group) (number of responses in vehicle group)

Student's t-test was used for statistical analysis to determine the significance of compound effects. Data are reported as a dose that yielded a % inhibition of a response.

Test C: Neuropathic pain model (Chronic Constriction Injury);

The anti-hyperalgesia properties of a compound may be tested with the Chronic Constriction Injury ("CCI") model. The test is a model for neuropathic pain associated with nerve injuries that can arise directly from trauma and compression, or indirectly from a wide range of diseases such as infection, cancer, metabolic conditions, toxins, nutritional deficiencies, immunological dysfunction, and musculoskeletal changes. In the model a unilateral peripheral hyperalgesia is produced in rats by nerve ligation (G. J. Bennett, et al., *Pain* 33, 87–107 (1988)).

Procedurally, Sprague-Dawley rats (250–350 g) are anesthetized with sodium pentobarbital and the common sciatic nerve is exposed at the level of the mid thigh by blunt dissection through the biceps femoris. A section of nerve (about 7 mm), proximal to the sciatic trifucation, is freed of tissue and ligated at four positions with chromic gut suture. The suture is tied with about 1 mm spacing between ligatures. The incision is closed in layers and the animals are allowed to recuperate. Thermal hyperalgesia is measured using a paw-withdrawal test (K. Hargreaves, et al., *Pain* 32, 77–88 (1988)). To perform the test, animals are habituated on an elevated glass floor. A radiant heat source is aimed at the mid-plantar hindpaw (sciatic nerve territory) through the glass floor with a 20 second cut-off used to prevent injury to the skin. The latencies for the withdrawal reflex in both hind paws are recorded.

Injured paws with ligated nerves show shorter paw withdrawal latencies compared to the uninjured or sham operated paws. Responses to test compounds are evaluated at different times after oral administration to determine the onset and duration of compound effect. When performing the test, groups of CCI rats receive either vehicle or the test compound orally three times daily for 5 days. Paw withdrawal latencies are measured each day 10 min before and 2 or 3 hr. after the first daily dose. Compound efficacy is expressed as mean percentage decrease of hyperalgesia compared to that of vehicle-treated animals, calculated as follows:

$$\frac{(\text{Mean of vehicle group} - \text{Mean of compound group})}{(\text{Mean of vehicle group})} \times 100$$

Data analysis was performed by the multiple means comparison test (Dunnett's test) and results are expressed and compound potencies are expressed as the MED (minimum effective dose), in mg/Kg/day, that yields a percent (%) decrease in hyperalgesia that is statistically significant.

Table 3 shows the results of tests A, B and C. Where no data is provided that test was not performed.

TABLE 3

| Example No. | Test A Ki (nM) | Test B First phase Dose (% Inh.) | Test B Second phase Dose (% Inh.) | Test C MED (% Inh.) |
|---|---|---|---|---|
| Ex. 1 | 194 | 173 (50%) | 65 (50%) 200 (68%) | 5 (61%) |
| Ex. 2 | 3400 | | | 30 (76%) |
| Ex. 3 | 282 | 200 (83%) | 200 (72%) | 15 (56%) |

What is claimed is:

1. 7-chloro-4,10-dihydroxy-2-(1-pyridin-2-yl-ethyl)-2H-pyridazino[4,5-b]quinolin-1-one and pharmaceutically-acceptable salts thereof.

2. 7-chloro-4,10-dihydroxy-2-((S)-1-pyridin-2-yl-ethyl)-2H-pyridazino[4,5-b]quinolin-1-one and pharmaceutically-acceptable salts thereof.

3. A method for treating pain, said method comprising administration to a subject experiencing pain a pain-ameliorating effective amount of the compound according to claim 2.

4. A pharmaceutical composition comprising a compound according to claim 2 as an active ingredient together with one or more pharmaceutically-acceptable additives.

* * * * *